United States Patent
Arai

(10) Patent No.: US 9,638,650 B2
(45) Date of Patent: May 2, 2017

(54) PIEZOELECTRIC ELEMENT FEEDER CAPABLE OF MEASURING ELECTRIC CHARACTERISTICS OF PIEZOELECTRIC ELEMENT AND METHOD OF MEASURING ELECTRIC CHARACTERISTICS OF PIEZOELECTRIC ELEMENT

(71) Applicant: NHK SPRING CO., LTD., Yokohama-shi, Kanagawa (JP)

(72) Inventor: Mikio Arai, Kanagawa (JP)

(73) Assignee: NHK Spring Co., Ltd., Kanagawa (JP)

( * ) Notice: Subject to any disclaimer, the term of this patent is extended or adjusted under 35 U.S.C. 154(b) by 115 days.

(21) Appl. No.: 14/017,859

(22) Filed: Sep. 4, 2013

(65) Prior Publication Data
US 2014/0077793 A1 Mar. 20, 2014

(30) Foreign Application Priority Data

Sep. 14, 2012 (JP) ................... 2012-203127

(51) Int. Cl.
*G01N 27/00* (2006.01)
*H01L 41/25* (2013.01)

(52) U.S. Cl.
CPC ............. *G01N 27/00* (2013.01); *H01L 41/25* (2013.01); *Y10T 29/42* (2015.01)

(58) Field of Classification Search
CPC .......... G01N 27/00; H01L 41/25; Y10T 29/42
USPC .................. 324/109, 754; 360/244, 245, 135
See application file for complete search history.

(56) References Cited

U.S. PATENT DOCUMENTS

| | | | |
|---|---|---|---|
| 4,494,902 A | 1/1985 | Kuppens et al. | |
| 6,340,858 B1* | 1/2002 | Jaenker | H01L 41/042 310/316.01 |
| 6,501,625 B1* | 12/2002 | Boismier | G11B 5/4846 360/294.7 |
| 6,556,028 B1 | 4/2003 | Umanskiy et al. | |
| 6,639,411 B1 | 10/2003 | Thomsen | |
| 7,642,523 B1* | 1/2010 | Devitt | H01J 37/18 250/440.11 |
| 8,598,524 B2* | 12/2013 | Persoon | H01J 37/185 250/310 |
| 2002/0036514 A1* | 3/2002 | Taura | G01R 31/2886 324/754.2 |
| 2003/0076121 A1 | 4/2003 | Guo et al. | |

(Continued)

FOREIGN PATENT DOCUMENTS

| | | |
|---|---|---|
| JP | 50-120272 | 9/1975 |
| JP | 59069926 A * | 4/1984 |

(Continued)

*Primary Examiner* — Son Le
*Assistant Examiner* — Akm Zakaria
(74) *Attorney, Agent, or Firm* — Norris McLaughlin & Marcus, P.A.

(57) ABSTRACT

A piezoelectric element feeder for feeding a piezoelectric element, includes a drawing unit that draws a first electrode surface of the piezoelectric element with use of negative pressure and transfers the piezoelectric element onto the actuator attaching part and a probe movably supported with the drawing unit and used to measure electric characteristics of the piezoelectric element. A front end of the probe is brought into contact with the first electrode surface when or just before the drawing unit draws the first electrode surface, to enable a measurement of the electric characteristics of the piezoelectric element.

12 Claims, 7 Drawing Sheets

(56) References Cited

U.S. PATENT DOCUMENTS

| | | | |
|---|---|---|---|
| 2004/0221465 A1* | 11/2004 | Smith | G01B 5/20 33/551 |
| 2006/0097162 A1* | 5/2006 | Maruyama | G01Q 10/04 250/309 |
| 2008/0310052 A1* | 12/2008 | Strom | G11B 9/02 360/135 |
| 2009/0042323 A1* | 2/2009 | Kasukabe | G01R 1/07342 438/17 |
| 2010/0085663 A1* | 4/2010 | Ando | G11B 5/4826 360/244.2 |
| 2010/0232069 A1* | 9/2010 | Hata | G11B 5/4826 360/245.4 |
| 2011/0149440 A1* | 6/2011 | Uematsu | G11B 5/4826 360/245.3 |
| 2012/0127614 A1 | 5/2012 | Arai | |
| 2012/0224282 A1* | 9/2012 | Hanya | G11B 5/4826 360/244.2 |
| 2012/0235697 A1* | 9/2012 | Jang | G01R 31/2886 324/754.03 |

FOREIGN PATENT DOCUMENTS

| | | |
|---|---|---|
| JP | 61-93966 | 5/1986 |
| JP | 62-21037 | 5/1987 |
| JP | 63-83667 | 6/1988 |
| JP | 63-128727 | 6/1988 |
| JP | 63-184348 | 7/1988 |
| JP | 63-232168 | 9/1988 |
| JP | 63-249061 | 10/1988 |
| JP | 2-2898 | 1/1990 |
| JP | 6-120094 | 4/1994 |
| JP | 11-64414 | 3/1999 |
| JP | 2005-127752 | 5/2005 |
| JP | 2010-86649 | 4/2010 |
| JP | 2012-113782 | 6/2012 |

* cited by examiner

FIG.3
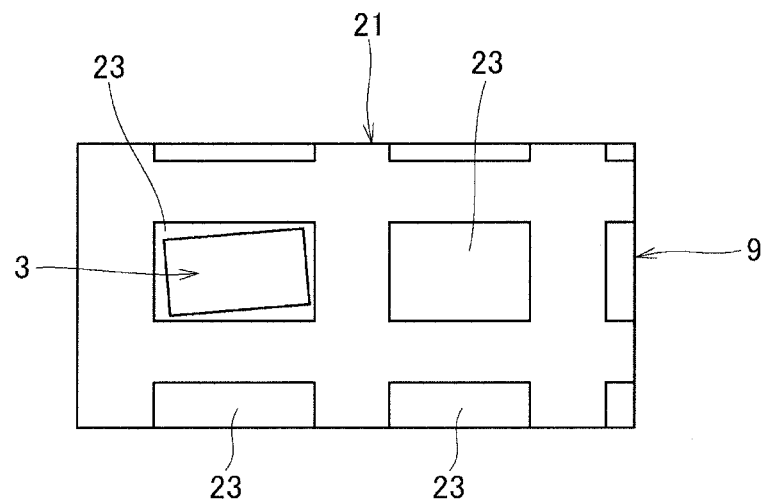
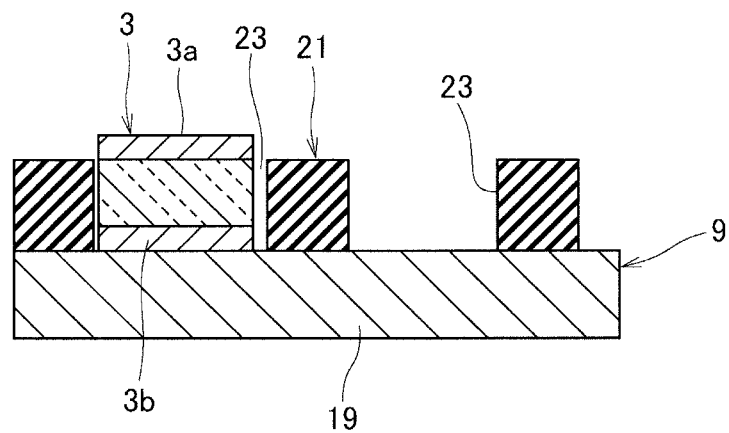
FIG.4A
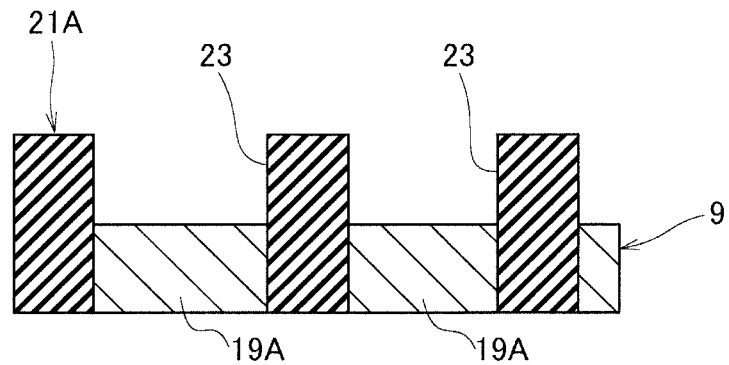
FIG.4B

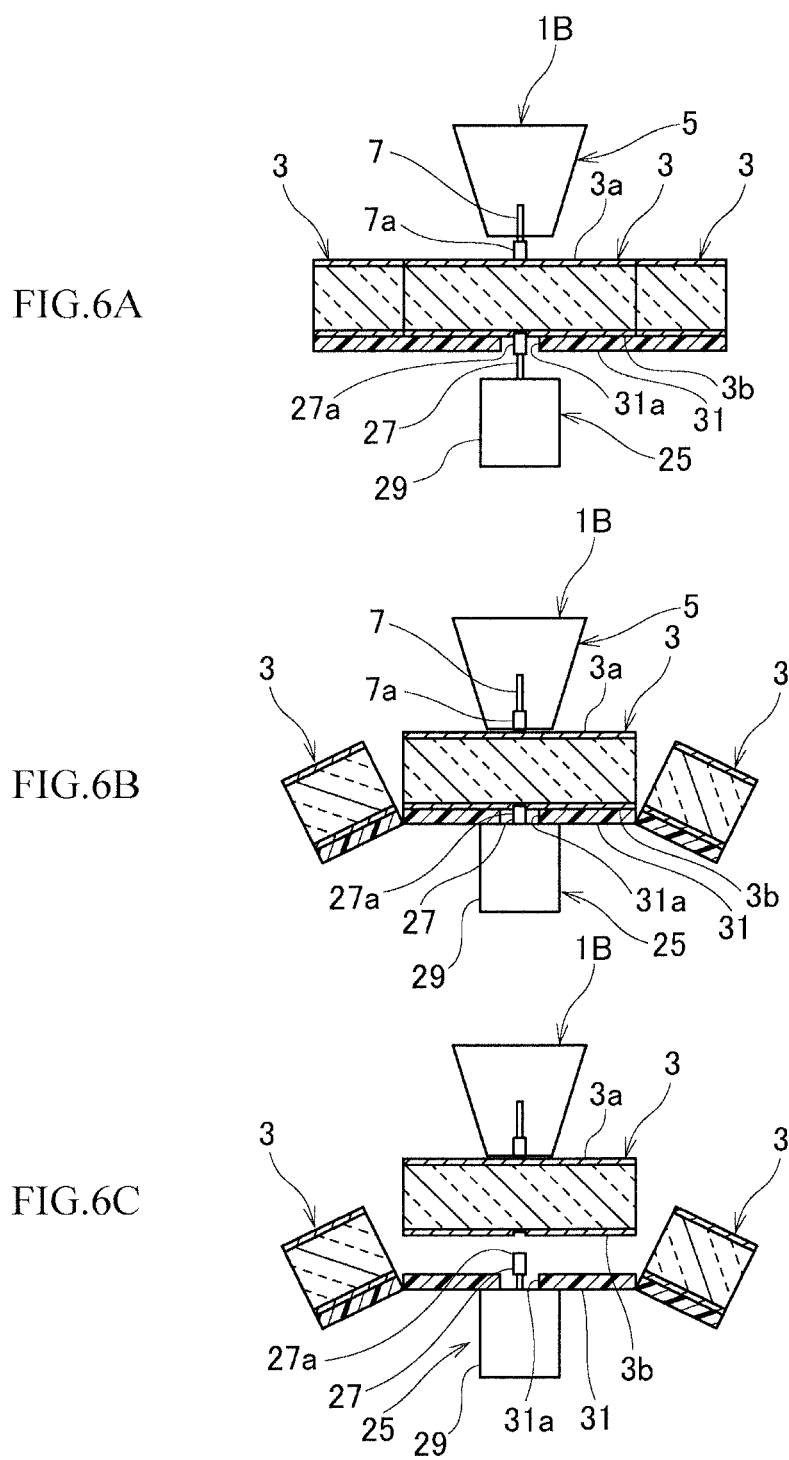

INSTALLED IN HDD

HEAD SUSPENSION ALONE IN FREE STATE

PIEZOELECTRIC ELEMENT FEEDER CAPABLE OF MEASURING ELECTRIC CHARACTERISTICS OF PIEZOELECTRIC ELEMENT AND METHOD OF MEASURING ELECTRIC CHARACTERISTICS OF PIEZOELECTRIC ELEMENT

BACKGROUND OF THE INVENTION

1. Field of the Invention

The present invention relates to a piezoelectric element feeder and a method of measuring electric characteristics of a piezoelectric element, the piezoelectric element feeder and the method used when manufacturing, for example, a head suspension being a device installed in a hard disk drive of an information processing apparatus such as a personal computer.

2. Description of Related Art

Recent hard disk drives are required to have very large capacity. To realize this, the number of tracks per inch (TPI) on a hard disk in the hard disk drive becomes more and more increased to narrow the width of each track. To access such narrow tracks, there is a need for an actuator that is capable of precisely positioning a head of a head suspension within a minute range across the tracks.

To meet the need, the applicant of the present invention has proposed in Japanese Unexamined Patent Application Publication No. 2010-86649 a head suspension employing a dual actuator system. The dual actuator system uses a piezoelectric element in addition to a usual voice coil motor that drives a carriage to which the head suspension is attached. The piezoelectric element is arranged between a base plate and load beam of the head suspension, to finely move the head attached to the load beam relative to the base plate.

FIG. 9A is a plan view roughly illustrating a head suspension 101 according to a related art (Japanese Unexamined Patent Application Publication No. 2012-11378). FIG. 9B is an equivalent circuit of piezoelectric elements installed in the head suspension 101 of FIG. 9A, and FIG. 9C illustrates deformation of the piezoelectric elements.

The head suspension 101 has a base plate 103, a load beam 105, and the pair of piezoelectric elements 107a and 107b. The piezoelectric elements 107a and 107b are arranged between the base plate 103 and the load beam 105, are oppositely oriented, and are arranged in parallel with each other to form an actuator 109. A front end of the load beam 105 supports a read/write head 111 that is movable with the load beam 105 relative to the base plate 103.

The piezoelectric elements 107a and 107b oppositely deform according to a voltage applied thereto. Namely, one of the piezoelectric elements 107a and 107b expands and the other contracts, to slightly move the head 111 with the load beam 105 relative to the base plate 103 in a sway direction, i.e., a width direction of the head suspension 101 in which the piezoelectric elements 107a and 107b are arranged side by side.

For this structure and operation, the piezoelectric elements 107a and 107b must be attached to the head suspension 101 as correctly as designed.

The pair of piezoelectric elements 107a and 107b have the same appearance, and therefore, are hardly distinguishable from each other or between the back and front of each. Due to this, there is a risk of shipping the head suspension 101 with the piezoelectric elements 107a and 107b incorrectly installed.

To avoid such trouble, there is an idea of imprinting marks on the piezoelectric elements 107a and 107b to distinguish them from each other or between the back and the front. This technique, however, produces contaminants, and therefore, is impracticable.

There is another idea to apply voltage to the actuator 109 measure an actual stroke of the head 111, and determine if the piezoelectric elements 107a and 107b are correctly installed. The actual stroke of the head 111 is in the range of 50 to 100 nanometers, and therefore, this technique needs precision measuring equipment that is expensive.

U.S. Pat. No. 6,639,411 teaches a method of detecting whether or not piezoelectric elements of a head suspension are correctly oriented or have any defects according to signals that are obtained by forcibly displacing the head suspension.

FIG. 10A illustrates the head suspension 101 of FIG. 9A installed in a hard disk drive and FIG. 10B illustrates the head suspension 101 in a free state. As is apparent from comparison between FIGS. 10A and 10B, load on the load beam 105 of the head suspension 101 differs between the installed state of FIG. 10A and the free state of FIG. 10B. If, in the free state of FIG. 10B, a voltage is applied to test the piezoelectric elements 107a and 107b, only unstable data will be provided because the movement of the load beam 105 is unstable or variable in the free state of FIG. 10B. With such unstable data, the technique of the U.S. Pat. No. 6,639,411 is unable to determine whether or not the piezoelectric elements 107a and 107b are correctly installed.

There is another problem that a circuit breakage of the actuator 109, if any, is hardly detectable.

To solve these problems, the applicant of the present invention has proposed in the Japanese Unexamined Patent Application Publication No. 2012-113782 a method of testing piezoelectric elements according to C-V characteristics thereof. This method tests a finished head suspension into which a piezoelectric element is installed, and therefore, involves a problem that, if the piezoelectric element is tested as defective, the head suspension as a whole is accordingly defective by necessity.

Accordingly, there is a need for testing a piezoelectric element before its installation in a head suspension, to reduce defective head suspensions.

SUMMARY OF THE INVENTION

An object of the present invention is to provide a piezoelectric element feeder and a method of measuring electric characteristics of a piezoelectric element, capable of testing a piezoelectric element just before installing the same in an object such as a head suspension.

In order to accomplish the object, a first aspect of the present invention provides a piezoelectric element feeder for feeding a piezoelectric element, which is ready to be installed in an actuator attaching part, onto the actuator attaching part. The piezoelectric element feeder includes a drawing unit that draws a first electrode surface of the piezoelectric element with use of negative pressure and transfers the piezoelectric element onto the actuator attaching part and a probe that is movably supported with the drawing unit and is used to measure electric characteristics of the piezoelectric element. A front end of the probe is brought into contact with the first electrode surface when or just before the drawing unit draws the first electrode surface, to enable a measurement of the electric characteristics of the piezoelectric element.

A second aspect of the present invention provides a method of measuring electric characteristics of a piezoelectric element with use of the piezoelectric element feeder of the first aspect. The method includes placing the piezoelectric element in a waiting unit connected to an electric characteristic measuring device to put the piezoelectric element ready to be installed in an actuator attaching part so that a second electrode surface of the piezoelectric element is electrically connected to the waiting, bringing the front end of the probe that is electrically connected to the electric characteristic measuring device into contact with the first electrode surface of the piezoelectric element when or just before the drawing unit draws the first electrode surface, and measuring electric characteristics of the piezoelectric element with the electric characteristic measuring device.

A third aspect of the present invention provides a piezoelectric element feeder for feeding a piezoelectric element, which is ready to be installed in an actuator attaching part, onto the actuator attaching part. The piezoelectric element feeder includes a drawing unit that draws a first electrode surface of the piezoelectric element with use of negative pressure and transfers the piezoelectric element onto the actuator attaching part, a first probe that is movably supported with the drawing unit and is used to measure electric characteristics of the piezoelectric element, a lifter that is arranged so as to correspond to the drawing unit, and a second probe that is movably supported with the lifter and is used to measure the electric characteristics of the piezoelectric element. A front end of the first probe is brought into contact with the first electrode surface when or just before the drawing unit draws the first electrode surface. A front end of the second probe is brought into contact with a second electrode surface of the piezoelectric element when or just before the lifter lifts the second electrode surface according to the drawing of the first electrode surface. Then, a measurement of the electric characteristics of the piezoelectric element is realized.

A fourth aspect of the present invention provides a method of measuring electric characteristics of a piezoelectric element with use of the piezoelectric element feeder of the third aspect. The method includes readying the piezoelectric element to be installed onto an actuator attaching part by leaving the piezoelectric element on a film after dicing the piezoelectric element from a piezoelectric element mother material removably attached to the film, bringing the front end of the first probe that is electrically connected to the electric characteristic measuring device into contact with a first electrode surface of the piezoelectric element when or just before the drawing unit draws the first electrode surface, bringing the front end of the second probe that is electrically connected to the electric characteristic measuring device into contact with a second electrode surface of the piezoelectric element when or just before the lifter lifts the second electrode surface according to the drawing of the first electrode surface, and measuring electric characteristics of the piezoelectric element with the electric characteristic measuring device.

According to any one of the first and third aspects, the piezoelectric element feeder is capable of measuring electric characteristics of a piezoelectric element with a simple structure just before installing the piezoelectric element in an object such as a head suspension.

According to any one of the second and fourth aspects, the method surely measures electric characteristics of a piezoelectric element before installing the piezoelectric element in an object such as a head suspension.

BRIEF DESCRIPTION OF THE DRAWINGS

FIG. 3 is a plan view partly illustrating a feed tray used as a waiting unit for the piezoelectric element feeder;

FIGS. 4A and 4B are sectional views partly illustrating examples of the feed tray;

FIGS. 5A and 5B illustrate contact timing of a probe of the piezoelectric element feeder, in which FIG. 5A is a state that the probe is brought into contact with the piezoelectric element just before the feeder draws the piezoelectric element and FIG. 5B is a state that the piezoelectric element is drawn by the feeder;

FIGS. 6A to 6C are sectional views illustrating a piezoelectric element feeder and a method of measuring electric characteristics of a piezoelectric element according to a second embodiment of the present invention, in which FIG. 6A illustrates a diced piezoelectric element with first and second probes brought into contact with first and second electrode surfaces, FIG. 6B illustrates the diced piezoelectric element with the first electrode surface drawn by a drawing unit of the feeder and the second electrode surface lifted by a lifter, and FIG. 6C illustrates the piezoelectric element drawn by the drawing unit away from a film;

FIGS. 9A to 9C are views illustrating a head suspension according to a related art, in which FIG. 9A is a plan view of the head suspension, FIG. 9B is an equivalent circuit diagram of piezoelectric elements of the head suspension, and FIG. 9C illustrates deformation of the piezoelectric elements; and FIGS. 10A and 10B schematic side views illustrating the head suspension of the related art, in which FIG. 10A illustrates the head suspension installed in a hard disk drive and FIG. 10B illustrates the head suspension alone in a free supported state.

DETAILED DESCRIPTION OF EMBODIMENTS

Figure 1:
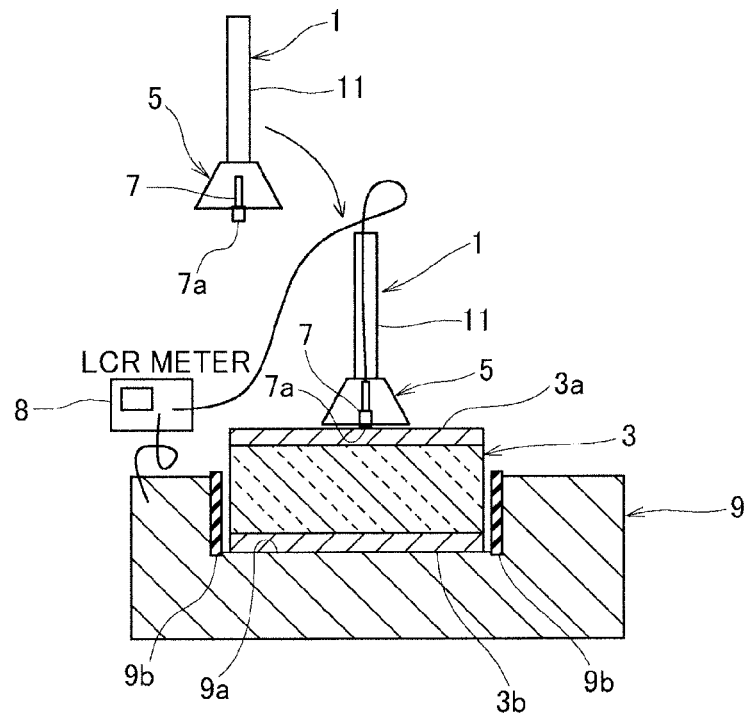
FIG. 1 is a general view illustrating a piezoelectric element feeder and a method of measuring electric characteristics of a piezoelectric element according to a first embodiment of the present invention.

A piezoelectric element feeder and a method of measuring electric characteristics of a piezoelectric element according to embodiments of the present invention will be explained with reference to drawings.

The piezoelectric element feeder 1 or 1B (FIG. 1 or 6) and the method of measuring electric characteristics of the piezoelectric element 3 that uses the piezoelectric element feeder are capable of testing a piezoelectric element 3 just before installing the same in a head suspension. For this, the piezoelectric element feeder 1 or 1B feeds a piezoelectric element 3, which is ready to be installed in an actuator attaching part, onto an actuator attaching part and includes a drawing unit 5 that draws a first electrode surface 3a of the piezoelectric element 3 with the use of negative pressure and transfers the piezoelectric element 3 onto the actuator attaching part and a probe 7 movably supported with the drawing unit 5 and used to measure electric characteristics of the piezoelectric element. A front end 7a of the probe 7 is brought into contact with the first electrode surface 3a when or just before the drawing unit 5 draws the first electrode surface 3a, to enable a measurement of electric characteristics of the piezoelectric element 3.

Hereinafter, the piezoelectric element feeder 1 and the method of measuring electric characteristics of the piezoelectric element 3 according to the first embodiment will be explained in detail.

FIG. 1 is a general view illustrating the piezoelectric element feeder 1 and a method of measuring electric characteristics of the piezoelectric element 3 according to the first embodiment.

The piezoelectric element feeder 1 has the drawing unit 5 that draws the first electrode surface 3a of the piezoelectric element 3 with the use of negative pressure and transfers and installs the piezoelectric element 3 onto an actuator attaching part. The piezoelectric element 3 is ready to be installed in the actuator attaching part at a waiting unit 9. The drawing unit 5 movably supports the probe 7 that is used to measure electric characteristics of the piezoelectric element 3. When the probe 7 is in a free state as illustrated at the upper left of FIG. 1, the front end 7a of the probe 7 protrudes from the drawing unit 5.

Two piezoelectric element feeders 1 illustrated at the upper left and center of FIG. 1 represent respective states of the single piezoelectric element feeder 1 before and after drawing the piezoelectric element 3. Namely, one of them is imaginary in FIG. 1.

Figure 9A:
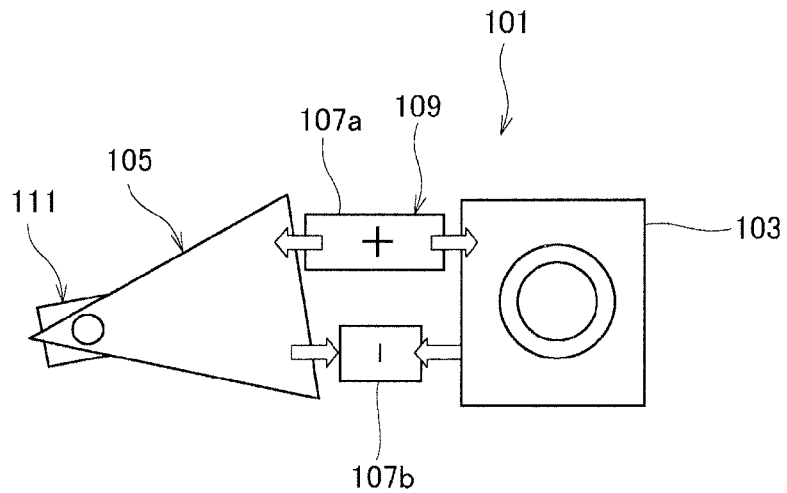
Figure 9B:
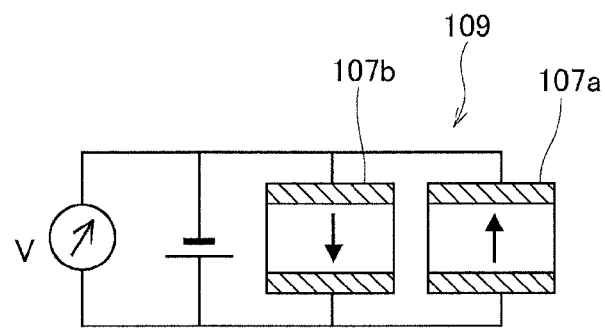
Figure 9C:
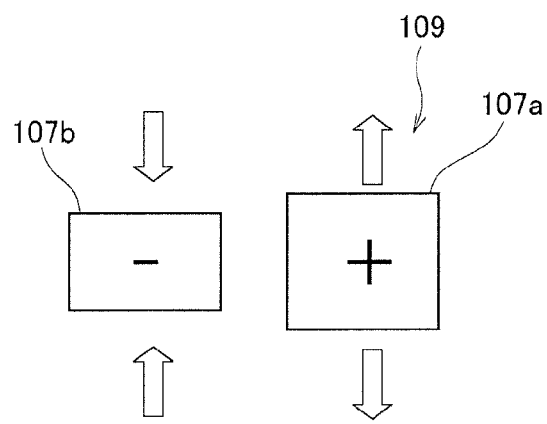
Figure 10A:
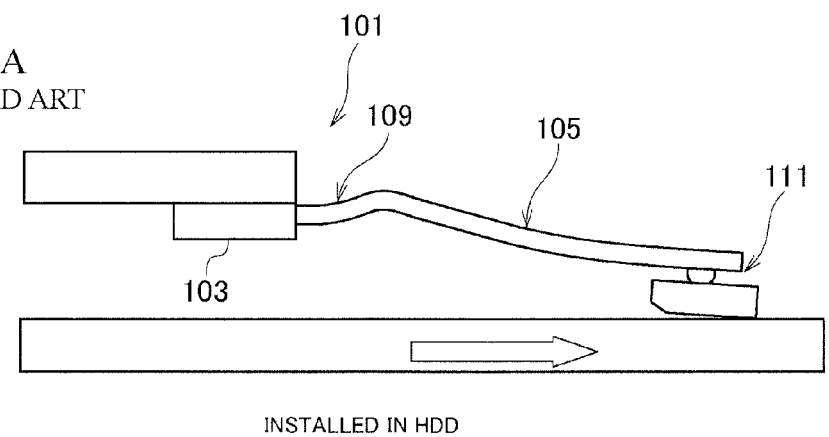
Figure 10B:
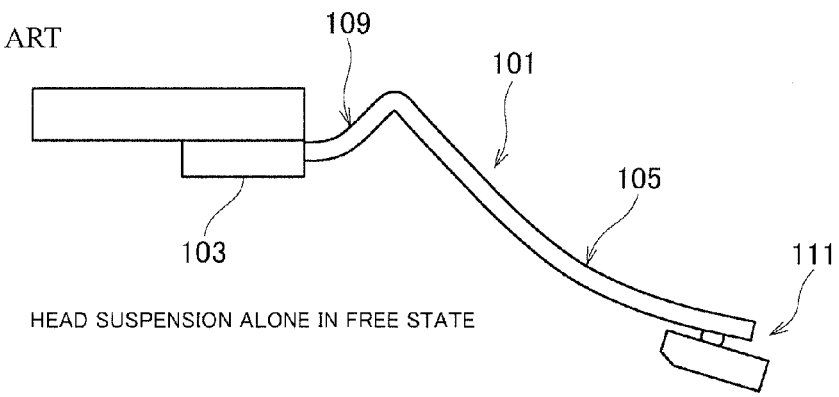

The actuator attaching part in which the piezoelectric element 3 is installed exists on, for example, a head suspension like the related art of FIG. 9A. The head suspension has a base plate and a load beam, and between the base plate and the load beam, there is the actuator attaching part in which a pair of piezoelectric elements are arranged in opposite orientations to form an actuator. A front end of the load beam supports a read/write head that is moved with the load beam relative to the base plate when the piezoelectric elements are energized and deformed. The actuator may have only one piezoelectric element instead of two.

The piezoelectric element 3 to be installed in the actuator attaching part is set in a waiting unit 9 and is put ready to be installed in the actuator attaching part so that a second electrode surface 3b of the piezoelectric element 3 is electrically conductive or connected to the waiting unit 9. The waiting unit 9 is conductive and is connected to an LCR meter 8 serving as an electric characteristic measuring device. The LCR meter 8 is also connected to the probe 7.

The waiting unit 9 is, for example, a feed tray having an accommodation cell 9a and a partition wall 9b that is nonconductive and composes a side wall surrounding the accommodation cell 9a. The waiting unit 9 is used to put the piezoelectric element 3 ready to be installed in the actuator attaching part, and therefore, may take any form such as an intermediate stage instead of the feed tray. In this case, the intermediate stage includes a stage to align piezoelectric elements and is used like the feed tray.

Figure 2:
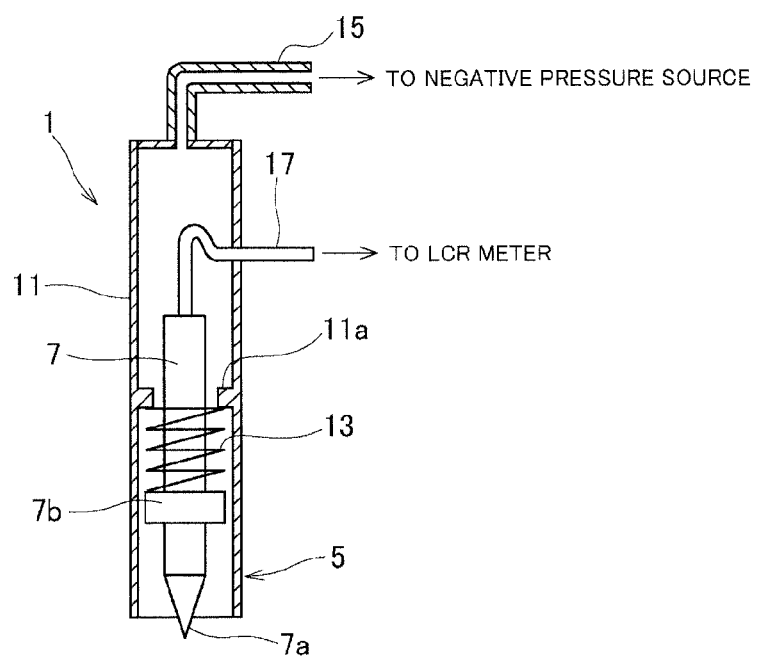
FIG. 2 is a sectional view illustrating the piezoelectric element feeder of FIG. 1.

FIG. 2 is a sectional view illustrating the piezoelectric element feeder 1 of FIG. 1.

The piezoelectric element feeder 1 has a cylindrical main body 11. The main body 11 incorporates a coil spring 13 serving as an elastic member that movably supports the probe 7. The coil spring 13 is arranged between an inner flange 11a of the main body 11 and a flange 7b of the probe 7. Negative pressure passes through an inner circumference of the inner flange 11a and an outer circumference of the flange 7b, to act in the drawing unit 5. Pushing force of the coil spring 13 is set to be sufficiently weaker than drawing force due to the negative pressure acting in the drawing unit 5.

The front end 7a of the probe 7 protrudes from the drawing unit 5 and is retractable against the pushing force of the coil spring 13. A protruding length or position of the probe 7 is determined by a donut-shaped or an annular member (not illustrated) attached or screwed to an inner face of the drawing unit 5, the annular member with which the flange 7b engages.

The coil spring 13 retractably pushes out the probe 7 so that the front end 7a of the probe 7 protrudes from the drawing unit 5 to resiliently come into contact with the first electrode surface 3a of the piezoelectric element 3. When the drawing unit 5 draws the piezoelectric element 3, the front end 7a of the probe 7 is pushed by the first electrode surface 3a so that the probe 7 retracts into the main body 11 against the pushing force of the coil spring 13 until the front end 7a of the probe 7 withdraws in the drawing unit 5.

This allows, when or just before the drawing unit 5 draws the piezoelectric element 3, the front end 7a of the probe 7 to be brought into contact with the first electrode surface 3a to enable a measurement of electric characteristics of the piezoelectric element 3.

The main body 11 of the piezoelectric element feeder 1 is connected through a flexible pipe 15 or the like to a negative pressure source such as a compressor. The probe 7 is connected through a harness 17 to the LCR meter 8. When the negative pressure source generates negative pressure acting in the drawing unit 15, a front end of the main body 11 serves as the drawing unit 5. The drawing unit 5 illustrated in FIG. 2 has a straight shape. It may have a horn shape as illustrated in FIG. 1.

FIG. 3 is a plan view illustrating the feed tray used as the waiting unit 9 and FIGS. 4A and 4B are sectional views illustrating examples of the feed tray 9. The example of FIG. 4A has a solid base and that of FIG. 4B has a base with divided base pieces.

As illustrated in FIGS. 3 to 4B, the feed tray 9 has a conductive base 19 or 19A, a nonconductive partition wall 21 or 21A, and accommodation cells 23 defined with the nonconductive partition wall on the conductive base to accommodate the respective piezoelectric elements 3. The accommodation cell 23 corresponds to the accommodation cell 9a in FIG. 1.

In the feed tray or waiting unit 9 of FIG. 4A, the base 19 serves as an electrode and is solid. The partition wall 21 is a lattice attached onto the base 19.

In the feed tray or waiting unit 9 of FIG. 4B, the base 19A serves as an electrode and is divided into base pieces corresponding to the respective accommodation cells 23. The partition wall 21A is a lattice and is taller than the partition wall 21 by the thickness of the base 19A. The divided base pieces of the base 19A are fitted into respective openings of the lattice of the partition wall 21A to define the accommodation cell 23. With this structure, the partition wall 21 has sections each interposed between corresponding adjacent divided base pieces to isolate them from one another.

In each of the feed trays or waiting units 9 of FIGS. 4A and 4B, the nonconductive partition wall 21 or 21A prevents an electric short circuit. In particular, the example of FIG. 4B isolates the divided base pieces of the base 19A serving as electrodes from one another for each of the piezoelectric elements 3 in the accommodation cells 23, to realize a more stable measurement of electric characteristics of the piezoelectric element 3 than the example of FIG. 4A.

When or just before the drawing unit 5 draws the piezoelectric element 3, the front end 7a of the probe 7 is brought into contact with the first electrode surface 3a of the piezoelectric element 3 and the LCR meter 8 measures electric characteristics of the piezoelectric element 3.

The electric characteristics to be measured include, for example, C-V characteristics like the Japanese Unexamined Patent Application Publication No. 2012-113782, to determine if a pair of piezoelectric elements are correctly arranged or if there is a wire breakage. In the case of a head suspension employing a single piezoelectric element, the electric characteristics to be measured include, for example, a C value to or a tangent delta loss.

Additionally, the sum of C values of two piezoelectric elements measured just before installation may be compared with the sum of C values of them measured after installation, to determine if the characteristics of the piezoelectric elements have changed or deteriorated during installation. This test may be carried out on every piezoelectric element.

After measuring the electric characteristics, the piezoelectric element 3 is drawn by the drawing unit 5 with the use of negative pressure. The drawing unit 5 with the piezoelectric element 3 is moved onto the actuator attaching part of a head suspension and the piezoelectric element 3 is installed in the actuator attaching part. These movements may be automated with the use of robots.

Figure 5A:
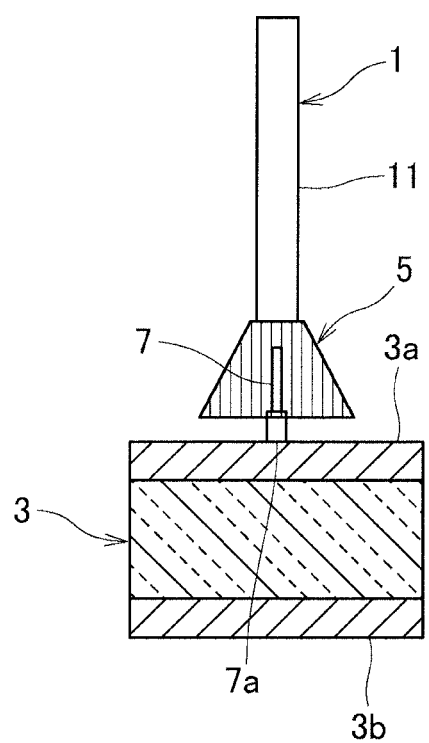
Figure 5B:
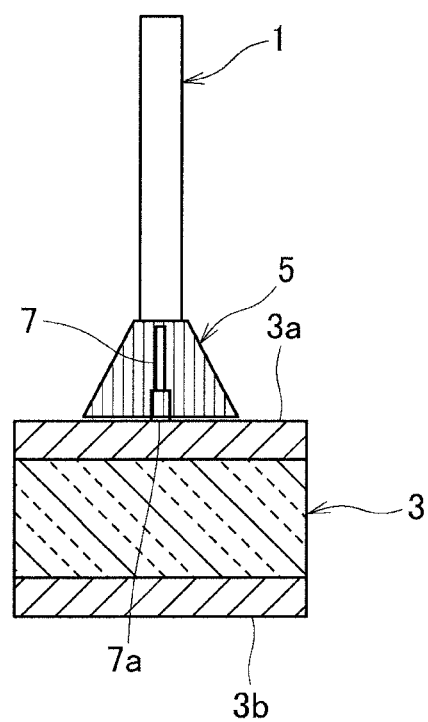

FIGS. 5A and 5B illustrate an example of the contact timing of the probe 7 with respect to the piezoelectric element 3. As illustrated in FIG. 5A, the front end 7a of the probe 7 protruding from the drawing unit 5 is brought into contact with the first electrode surface 3a of the piezoelectric element 3 just before the drawing unit 5 draws the piezoelectric element 3. In this state, electric characteristics of the piezoelectric element 3 are measured. Thereafter, as illustrated in FIG. 5B, the piezoelectric element 3 is drawn by the drawing unit 5. With such contact timing, electric characteristics of the piezoelectric element 3 are stably measurable.

In this way, the piezoelectric element feeder 1 for feeding the piezoelectric element 3, which is ready to be installed in the actuator attaching part, i.e., set in the waiting unit 9, onto the actuator attaching part according to the first embodiment includes the drawing unit 5 that draws and installs the first electrode surface 3a of the piezoelectric element 3 with the use of negative pressure and transfers the piezoelectric element 3 onto the actuator attaching part and the probe 7 that is movably supported with the drawing unit 5 and is used to measure electric characteristics of the piezoelectric element, the front end 7a of the probe 7 being brought into contact with the first electrode surface 3a just before the drawing unit 5 draws the first electrode surface 3a, to enable a measurement of electric characteristics of the piezoelectric element 3.

The piezoelectric element feeder 1 has a simple structure with the probe 7 arranged inside the drawing unit 5 and is capable of testing the electric characteristics of the piezoelectric element 3.

The piezoelectric element feeder 1 is used to transfer the piezoelectric element 3 for its installation from the feed tray (waiting unit 9) to the actuator attaching part of a head suspension, and therefore, is capable of testing the electric characteristics of the piezoelectric element 3 just before installing the piezoelectric element 3 in the head suspension, thereby reducing a percent defective of finished head suspensions.

The front end 7a of the probe 7 retractably protrudes from the drawing unit 5 with the spring force of the coil spring 13. The front end 7a is resiliently brought into contact with the first electrode surface 3a of the piezoelectric element 3 just before the drawing unit 5 draws the piezoelectric element 3. This makes it easy to measure the electric characteristics of the piezoelectric element 3 without special operations.

The piezoelectric element 3 to be attached to the actuator attaching part is set in the waiting unit 9 that is connected to the LCR meter 8. At this time, the second electrode surface 3b of the piezoelectric element 3 is electrically connected to the waiting unit 9. The LCR meter 8 is also connected to the probe 7. When or just before the drawing unit 5 draws the piezoelectric element 3, the front end 7a of the probe 7 is brought into contact with the first electrode surface 3a of the piezoelectric element 3, to measure electric characteristics of the piezoelectric element 3.

Accordingly, the electric characteristics of the piezoelectric element 3 are surely tested just before the piezoelectric element 3 is attached to the actuator attaching part. The electric characteristics testing is simplified because it is carried out during the attaching work of the piezoelectric element 3 to the actuator attaching part.

The feed tray serving as the waiting unit 9 has the conductive base 19 or 19A and nonconductive partition wall 21 or 21A to define the accommodation cells 23 that accommodate piezoelectric elements, respectively. The feed tray or waiting unit 9 allows the electric characteristics test of the piezoelectric element 3 to be surely carried out just before the installation of the piezoelectric element 3.

The base 19 of FIG. 4A is solid and the partition wall 21 is formed on the base 19. This feed tray is easy to be manufactured and is capable of preventing a short circuit over the piezoelectric elements in the respective accommodation cells 23.

The base 19A of FIG. 4B is divided into the base pieces corresponding to the respective cells 23 and the partition wall 21A has the sections each interposed between corresponding adjacent divided base pieces to isolate them from one another. This configuration realizes the more stable testing of electric characteristics of each piezoelectric elements in the cells 23.

Hereinafter, a piezoelectric element feeder and a method of measuring electric characteristics of a piezoelectric element according to the second embodiment of the present invention will be explained in detail with reference to FIGS. 6 to 8. The second embodiment is basically the same as the first embodiment, and therefore, like parts are represented with like reference numerals or like reference numerals plus "B" to omit overlapping explanations.

FIGS. 6A to 6C are sectional views illustrating a piezoelectric element feeder 1B and a method of measuring electric characteristics of a piezoelectric element 3 according to the second embodiment of the present invention, in which FIG. 6A illustrates the diced piezoelectric element 3 with first and second probes 7 and 27 brought into contact with first and second electrode surfaces 3a and 3b, FIG. 6B illustrates the diced piezoelectric element 3 with the first electrode surface 3a drawn by a drawing unit 5 of the feeder 1B and the second electrode surface 3b lifted by a lifter 25, and FIG. 6C illustrates the piezoelectric element 3 drawn by the drawing unit 5 away from a film 31.

The piezoelectric element feeder 1B according to the second embodiment has the drawing unit 5 to draw the first electrode surface 3a of the piezoelectric element 3, which is ready to be installed in the actuator attaching part, with the use of negative pressure and to transfer and install the piezoelectric element 3 onto an actuator attaching part of, for example, a head suspension, like the first embodiment. The drawing unit 5 movably supports a first probe 7 to measure electric characteristics of the piezoelectric element 3 like the first embodiment.

According to the second embodiment, a lifter 25 is arranged so as to correspond to the drawing unit 5. The lifter 25 movably supports a second probe 27 to measure the electric characteristics of the piezoelectric element 3.

The lifter 25 is, for example, a lifter pin having a cylindrical main body 29. The main body 29 contains a second coil spring serving as a second elastic member (not illustrated) to support the second probe 27, with a structure equal to the probe 7 of the first embodiment.

A front end 27a of the second probe 27 protrudes from the lifter 25 and is retractable therefrom against the spring force of the second coil spring. Accordingly, the front end 27a of the second probe 27 resiliently comes into contact with a second electrode surface 3b of the piezoelectric element 3 as explained later in detail.

When the lifter 25 lifts the piezoelectric element 3 as explained later in detail, the front end 27a of the second probe 27 is pushed by the second electrode surface 3b of the piezoelectric element 3 and retracts into the main body 29 against the spring force of the second coil spring. As a result, the front end 27a of the probe 27 withdraws inside the lifter 25.

When or just before the drawing unit 5 draws the first electrode surface 3a of the piezoelectric element 3, the front end 7a of the first probe 7 is brought into contact with the first electrode surface 3a, and when or just before the lifter 25 pushes the second electrode surface 3b of the piezoelectric element 3 upward according to the drawing of the first electrode surface 3a, the front end 27a of the second probe 27 is brought into contact with the second electrode surface 3b, to measure electric characteristics of the piezoelectric element 3.

Figure 7:
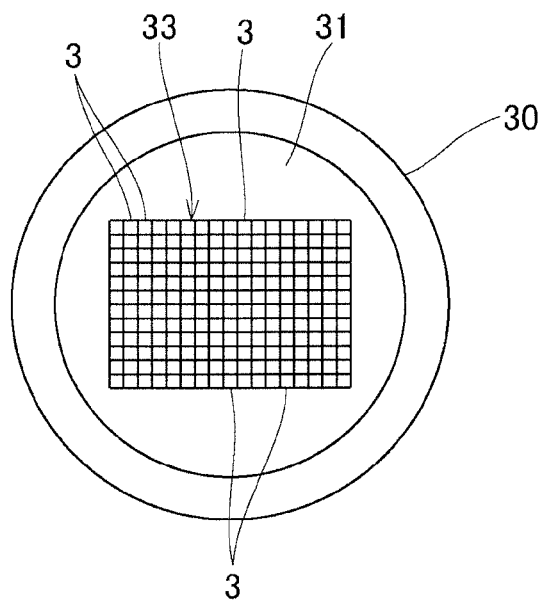
FIG. 7 is a plan view illustrating diced piezoelectric elements in a waiting state according to the second embodiment.
Figure 8:
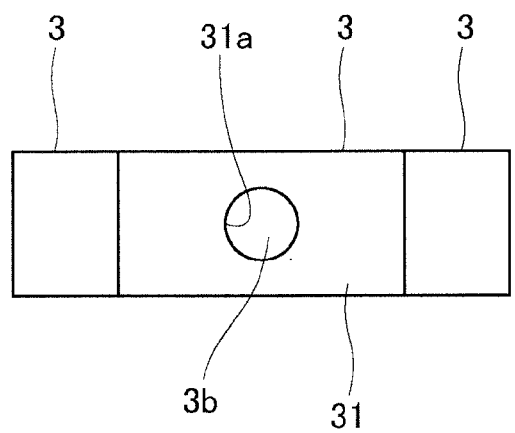
FIG. 8 is a back view partly illustrating a film and the diced piezoelectric elements of FIG. 7.

FIG. 7 is a plan view illustrating the diced piezoelectric elements 3 in a waiting state, and FIG. 8 is a back view illustrating the film 31 and the diced piezoelectric elements 3.

As illustrated in FIG. 7, the piezoelectric elements 3 to be attached to actuator attaching parts of head suspensions are formed from a piezoelectric mother material 33. The piezoelectric mother material 33 is removably attached to a film 31 by, for example, ultraviolet rays, the film 31 being supported with an annular frame 30. The piezoelectric mother material 33 is diced into the piezoelectric elements 3 each of which is left on the film 31 to wait for being transferred onto an actuator attaching part of a head suspension.

As illustrated in FIG. 8, the film 31 has a measurement hole 31a for every diced piezoelectric element 3, to expose a central portion of the second electrode surface 3b of the corresponding piezoelectric element 3. Through the measurement hole 31a, the front end 27a of the second probe 27 is brought into contact with the second electrode surface 3b.

The front end 27a of the probe 27 may be sharpened so that, without making the measurement hole 31a, the sharp front end 27a may pierce through the film 31 and come into contact with the second electrode surface 3b.

To feed the piezoelectric element 3 and measure electric characteristics thereof, the first and second probes 7 and 27 are connected to an LCR meter equal to the LCR meter 8 of FIG. 1. When or just before the drawing unit 5 draws the first electrode surface 3a of the piezoelectric element 3, the front end 7a of the first probe 7 is brought into contact with the first electrode surface 3a, and when or just before the lifter 25 pushes the second electrode surface 3b of the piezoelectric element 3 upward according to the drawing of the first electrode surface 3a, the front end 27a of the second probe 27 is brought into contact with the second electrode surface 3b, to measure electric characteristics of the piezoelectric element 3 with the LCR meter.

In FIG. 6A, the front end 7a of the first probe 7 is brought into contact with the first electrode surface 3a of the piezoelectric element 3 just before the drawing unit 5 draws the first electrode surface 3a of the piezoelectric element 3. At the same time, just before the lifter 25 lifts the second electrode surface 3b of the piezoelectric element 3 according to the drawing of the first electrode surface 3a by the drawing unit 5, the front end 27a of the second probe 27 is brought into contact with the second electrode surface 3b through the measurement hole 31a of the film 31. Then, the LCR meter measures electric characteristics of the piezoelectric element 3.

In FIG. 6B, the drawing unit 5 is lowered to draw the first electrode surface 3a after the measurement of the electric characteristics of the piezoelectric element 3. In synchronization with the movement of the drawing unit 5, the lifter 25 is ascended to come into contact with the second electrode surface 3b through the film 31. With the drawing unit 5 and lifter 25 holding the piezoelectric element 3, the lifter 25 pushes the piezoelectric element 3 upward, and in synchronization with this, the drawing unit 5 is ascended. As a result, the piezoelectric element 3 held by the drawing unit 5 and lifter 25 is separated from the adjacent piezoelectric elements.

In FIG. 6C, the lifter 25 is stopped ascending and the drawing unit 5 is continuously ascended to remove the piezoelectric element 3 from the film 31.

Thereafter, the drawing unit 5 is moved to the actuator attaching part and the piezoelectric element 3 is installed in the actuator attaching part. These movements may be automated with the use of robots.

In this way, the piezoelectric element feeder 1B for feeding the piezoelectric element 3, which is ready to be installed in an actuator attaching part, onto the actuator attaching part according to the second embodiment includes the drawing unit 5 that draws the first electrode surface 3a of the piezoelectric element 3 with the use of negative pressure and transfers and installs the piezoelectric element 3 onto the actuator attaching part, the first probe 7 that is movably supported with the drawing unit 5 and is used to measure electric characteristics of the piezoelectric element 3, the lifter 25 that is arranged so as to correspond to the drawing unit 5, and the second probe 27 that is movably supported with the lifter 25 and is used to measure the electric characteristics of the piezoelectric element 3. The front end 7a of the first probe 7 is brought into contact with the first electrode surface 3a when or just before the drawing unit 5 draws the first electrode surface 3a. The front end 27a of the second probe 27 is brought into contact with the second electrode surface 3b of the piezoelectric element 3 when or just before the lifter 25 lifts the second electrode surface 3b according to the drawing of the first electrode surface 3a. This enables a measurement of electric characteristics of the piezoelectric element 3.

The second embodiment simply arranges the first probe 7 in the drawing unit 5 and the second probe 27 in the lifter 25, to realize a measurement of electric characteristics of the piezoelectric element 3.

The drawing unit 5 directly transfers the diced piezoelectric element 3 for installation onto the actuator attaching part of a head suspension. Accordingly, the electric characteristics of the piezoelectric element 3 can be tested just before installing the piezoelectric element 3 in the head suspension, thereby reducing a percent defective of finished head suspensions.

The front end 7*a* of the first probe 7 retractably protrudes from the drawing unit 5 with spring force of the first coil spring serving as a first elastic member. The front end 27*a* of the second probe 27 retractably protrudes from the lifter 25 with spring force of the second coil spring. The front ends 7*a* and 27*a* of the first and second probes 7 and 27 are resiliently brought into contact with the first and second electrode surfaces 3*a* and 3*b* of the piezoelectric element 3, respectively.

This allows the front end 7*a* of the first probe 7 to come into contact with the first electrode surface 3*a* just before the drawing unit 5 draws the piezoelectric element 3, and allows the front end 27*a* of the second probe 27 to come into contact with the second electrode surface 3*b* just before the lifter 25 lifts the second electrode surface 3*b* of the piezoelectric element 3 according to the drawing of the piezoelectric element 3 by the drawing unit 5. This makes it easy to measure electric characteristics of the piezoelectric element 3 without special operations.

The piezoelectric element 3 to be attached to the actuator attaching part of a head suspension is diced from the piezoelectric mother material 33 that is removably bonded to the film 31. The diced piezoelectric element 3 is left on the film 31 and waits to be transferred to the actuator attaching part. The first and second probes 7 and 27 are connected to the LCR meter 8. Just before the drawing unit 5 draws the piezoelectric element 3, the front end 7*a* of the first probe 7 is brought into contact with the first electrode surface 3*a* of the piezoelectric element 3. Just before the lifter 25 pushes up the second electrode surface 3*b* of the piezoelectric element 3 according to the drawing of the piezoelectric element 3 by the drawing unit 5, the front end 27*a* of the second probe 27 is brought into contact with the second electrode surface 3*b*. Then, electric characteristics of the piezoelectric element 3 are measured.

Accordingly, the electric characteristics of the piezoelectric element 3 are surely tested just before the piezoelectric element 3 is attached to the actuator attaching part. The electric characteristics testing is simplified because it is carried out during the attaching work of the piezoelectric element 3 to the actuator attaching part.

The piezoelectric element 3 to be attached to the actuator attaching part is diced from the piezoelectric mother material 33 that is removably attached to the film 31. The diced piezoelectric element 3 is left on the film 31 and waits to be transferred to the actuator attaching part. The electric characteristics testing is surely carried out just before directly transferring and installing the diced and waiting piezoelectric element to the actuator attaching part, i.e., during a installing process for the diced and waiting piezoelectric element to the actuator attaching part.

The film 31 has the measurement hole 31*a* to expose the second electrode surface 3*b* of the respective one of the diced piezoelectric elements 3. The second probe 27 is brought into contact with the second electrode surface 3*b* through the measurement hole 31*a*.

As a result, the second probe 27 is surely brought into contact with the second electrode surface 3*b* of the diced piezoelectric element 3. Accordingly, the second probe 27 may be a standard probe instead of a special one.

The measuring of electric characteristics of the piezoelectric element 3 with the probe 7 may be carries out at the time when the drawing unit 5 draws the piezoelectric element 3. The measuring of electric characteristics of the piezoelectric element 3 with the first and second probes 7 and 27 may be carried out at the time when the drawing unit 5 draws the first electrode surface 3*a* of the piezoelectric element 3 and when the lifter 25 lifts the second electrode surface 3*b* of the piezoelectric element 3 according to the drawing of the piezoelectric element 3 by the drawing unit 5.

The piezoelectric element feeder and the method of measuring electric characteristics of a piezoelectric element according to the present invention are applicable not only to piezoelectric element actuators of head suspensions but also to piezoelectric element actuators of other devices.

What is claimed is:

1. A piezoelectric element feeder for feeding a piezoelectric element, which is ready to be installed in an actuator attaching part, onto the actuator attaching part, comprising:
    a hollow cylindrical main body defining an internal space on which negative pressure acts;
    a drawing unit that is a hollow cylindrical part comprised of a front end of the main body and having an opening communicating with the internal space of the hollow cylindrical main body to draw a first electrode surface of the piezoelectric element by the negative pressure acting on the internal space of the main body while the drawing unit contacts the first electrode surface of the piezoelectric element along a periphery of the opening, and to convey the drawn piezoelectric element onto the actuator attaching part; and
    a probe supported in the internal space of the main body so as to be movable through the opening between a first position at which the probe protrudes from the internal space so that a front end of the probe is brought into contact with the first electrode surface when or just before the drawing unit draws the first electrode surface, to enable the measurement of electric characteristics of the piezoelectric element, and a second position at which the probe is retracted into the internal space.

2. The piezoelectric element feeder of claim 1, further comprising:
    an elastic member retractably pushing out the probe so that the front end of the probe protrudes from the drawing unit to resiliently come into contact with the first electrode surface of the piezoelectric element.

3. A method of measuring electric characteristics of a piezoelectric element with use of the piezoelectric element feeder of claim 1, comprising:
    placing the piezoelectric element in a waiting unit connected to an electric characteristic measuring device to put the piezoelectric element ready to be installed in an actuator attaching part so that a second electrode surface of the piezoelectric element is electrically connected to the waiting unit;
    bringing the front end of the probe that is electrically connected to the electric characteristic measuring device into contact with the first electrode surface of the piezoelectric element when or just before the drawing unit draws the first electrode surface; and
    measuring electric characteristics of the piezoelectric element with the electric characteristic measuring device.

4. The method of claim 3, wherein the waiting unit is a feed tray having a conductive base and a nonconductive partition wall that defines accommodation cells on the conductive base, the accommodation cells each accommodating the piezoelectric element.

5. The method of claim 4, wherein the base is a solid base and the partition wall is formed onto the solid base.

6. The method of claim 4, wherein the base is divided into base pieces corresponding to the respective accommodation cells and the partition wall has sections each interposed between corresponding adjacent divided base pieces to isolate the divided base pieces from one another.

7. A piezoelectric element feeder for feeding a piezoelectric element, which is ready to be installed in an actuator attaching part, onto the actuator attaching part, comprising:
a hollow cylindrical main body defining an internal space on which negative pressure acts;
a drawing unit that is a hollow cylindrical part comprised of a front end of the main body and having an opening communicating with the internal space of the hollow cylindrical main body to draw a first electrode surface of the piezoelectric element by the negative pressure acting on the internal space of the main body while the drawing unit contacts the first electrode surface of the piezoelectric element along a periphery of the opening, and to convey the drawn piezoelectric element onto the actuator attaching part;
a first probe movably supported in the internal space of the main body so as to be movable through the opening between a first position at which the probe protrudes from the internal space for measurement of electric characteristics of the piezoelectric element and a second position at which the probe is retracted into the internal space;
a lifter arranged so as to correspond to the drawing unit;
a second probe movably supported with the lifter for measurement of electric characteristics of the piezoelectric element; and
a front end of the first probe in the first position of the first probe being brought into contact with the first electrode surface when or just before the drawing unit draws the first electrode surface, a front end of the second probe being brought into contact with a second electrode surface of the piezoelectric element when or just before the lifter lifts the second electrode surface according to the drawing of the first electrode surface, to enable the measurement of the electric characteristics of the piezoelectric element.

8. The piezoelectric element feeder of claim 7, further comprising:
a first elastic member retractably pushing out the first probe so that the front end of the first probe protrudes from the drawing unit to resiliently come into contact with the first electrode surface of the piezoelectric element; and
a second elastic member retractably pushing out the second probe so that the front end of the second probe protrudes from the lifter to resiliently come into contact with the second electrode surface of the piezoelectric element.

9. A method of measuring electric characteristics of a piezoelectric element with use of the piezoelectric element feeder of claim 7, comprising:
readying the piezoelectric element to be installed onto an actuator attaching part by leaving the piezoelectric element on a film after dicing the piezoelectric element from a piezoelectric element mother material removably attached to the film;
bringing the front end of the first probe that is electrically connected to an electric characteristic measuring device into contact with a first electrode surface of the piezoelectric element when or just before the drawing unit draws the first electrode surface;
bringing the front end of the second probe that is electrically connected to the electric characteristic measuring device into contact with a second electrode surface of the piezoelectric element when or just before the lifter lifts the second electrode surface according to the drawing of the first electrode surface; and
measuring electric characteristics of the piezoelectric element with the electric characteristic measuring device through the first and second probes being into contact with the respective first and second electrode surfaces.

10. The method of claim 9, wherein the film has a measurement hole to expose the second electrode surface of the diced piezoelectric element and the second probe is brought into contact with the second electrode surface through the measurement hole.

11. The piezoelectric element feeder of claim 1, further comprising support structure for movably supporting the first probe in the internal space of the main body, the support structure comprising a first flange on an internal cylindrical surface of the hollow cylindrical part, a second flange on an external surface of the probe, the first and second flanges being axially spaced from each other, and a coil spring having axially opposite ends engaging the respective first and second flanges.

12. The piezoelectric element feeder of claim 7, further comprising support structure for movably supporting the first probe in the internal space of the main body, the support structure comprising a first flange on an internal cylindrical surface of the hollow cylindrical part, a second flange on an external surface of the probe, the first and second flanges being axially spaced from each other, and a coil spring having axially opposite ends engaging the respective first and second flanges.

* * * * *